US008821861B2

(12) United States Patent
Smith et al.

(10) Patent No.: US 8,821,861 B2
(45) Date of Patent: Sep. 2, 2014

(54) FIBRIN SEALANT

(75) Inventors: Stephanie A. Smith, Champaign, IL (US); James H. Morrissey, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 152 days.

(21) Appl. No.: 12/680,947

(22) PCT Filed: Oct. 2, 2008

(86) PCT No.: PCT/US2008/078584
§ 371 (c)(1),
(2), (4) Date: Jun. 21, 2010

(87) PCT Pub. No.: WO2009/046194
PCT Pub. Date: Apr. 9, 2009

(65) Prior Publication Data
US 2010/0284998 A1 Nov. 11, 2010

Related U.S. Application Data

(60) Provisional application No. 60/978,009, filed on Oct. 5, 2007.

(51) Int. Cl.
*A61K 38/48* (2006.01)
*A61K 38/43* (2006.01)

(52) U.S. Cl.
USPC .................................. 424/94.64; 424/94.1

(58) Field of Classification Search
USPC ............................................. 424/94.64, 94.1
See application file for complete search history.

(56) References Cited

U.S. PATENT DOCUMENTS

| | | | |
|---|---|---|---|
| 3,983,004 | A | 9/1976 | Trobisch et al. |
| 4,139,619 | A | 2/1979 | Chidsey, III |
| 4,416,812 | A | 11/1983 | Becker et al. |
| 4,684,635 | A | 8/1987 | Orentreich et al. |
| 4,784,944 | A | 11/1988 | Kolde |
| 4,865,984 | A | 9/1989 | Nemerson et al. |
| 4,874,766 | A | 10/1989 | Ooms et al. |
| 5,059,525 | A | 10/1991 | Bartl et al. |
| 5,169,786 | A | 12/1992 | Carroll et al. |
| 5,192,689 | A | 3/1993 | Hemker et al. |
| 5,254,350 | A | 10/1993 | Barrow et al. |
| 5,270,451 | A | 12/1993 | Hawkins et al. |
| 5,298,599 | A | 3/1994 | Rezaie et al. |
| 5,314,695 | A | 5/1994 | Brown |
| 5,338,538 | A | 8/1994 | Tricca et al. |
| 5,358,853 | A | 10/1994 | Butler et al. |
| 5,391,380 | A | 2/1995 | Barrow et al. |
| 5,418,141 | A | 5/1995 | Zweig et al. |
| 5,418,143 | A | 5/1995 | Zweig |
| 5,426,031 | A | 6/1995 | Hawkins et al. |
| 5,472,850 | A | 12/1995 | Morrissey |
| 5,504,067 | A | 4/1996 | Morrissey et al. |
| 5,504,193 | A | 4/1996 | Hawkins et al. |
| 5,508,170 | A | 4/1996 | Butler et al. |
| 5,510,077 | A * | 4/1996 | Dinh et al. ............... 264/485 |
| 5,512,304 | A | 4/1996 | Barrow et al. |
| 5,580,744 | A | 12/1996 | Zweig |
| 5,599,909 | A | 2/1997 | Fickenscher et al. |
| 5,625,036 | A | 4/1997 | Hawkins et al. |
| 5,632,727 | A | 5/1997 | Tipton et al. |
| 5,691,380 | A | 11/1997 | Mason et al. |
| 5,705,477 | A | 1/1998 | Sporn et al. |
| 5,741,658 | A | 4/1998 | Morrissey |
| 5,787,901 | A | 8/1998 | Wilson |
| 5,866,425 | A | 2/1999 | Woodhams et al. |
| 5,888,968 | A | 3/1999 | Chen et al. |
| 5,945,087 | A | 8/1999 | Nelson et al. |
| 5,968,528 | A | 10/1999 | Deckner et al. |
| 6,100,072 | A | 8/2000 | Brucato et al. |
| 6,187,347 | B1 | 2/2001 | Patterson et al. |
| 6,194,394 | B1 | 2/2001 | Hawkins |
| 6,248,353 | B1 | 6/2001 | Singh |
| 6,258,368 | B1 | 7/2001 | Beerse et al. |
| 6,261,803 | B1 | 7/2001 | Zander et al. |
| 6,319,896 | B1 | 11/2001 | Dorin et al. |
| 6,323,326 | B1 | 11/2001 | Dorin et al. |
| 6,355,858 | B1 | 3/2002 | Gibbins |
| 6,376,209 | B2 | 4/2002 | Wissel et al. |
| 6,391,609 | B1 | 5/2002 | Goldford |
| 6,432,657 | B1 | 8/2002 | Kikuchi et al. |
| 6,451,610 | B1 | 9/2002 | Gorman et al. |
| 6,509,050 | B1 | 1/2003 | Henson et al. |

(Continued)

FOREIGN PATENT DOCUMENTS

| | | |
|---|---|---|
| DE | 1617733 | 4/1971 |
| EP | 0 727 434 | 8/1996 |

(Continued)

OTHER PUBLICATIONS

Topart et al. (Tisseel vs tack staples as mesh fixation in totally extraperitoneal laparoscopic repair of groin hernias. Surg Endosc (2005) 19:724-727).*
Choi et al. (2010) "Phosphoramidate end labeling of inorganic polyphosphates: Facile manipulation of polyphosphate for investigating and modulating its biological activities," Biochemistry 49:9935-9941.
Choi et al. (2011) "Polyphosphate is a Cofactor for the Activation of Factor XI by Thrombin," Blood 118:6963-6970.
Müller et al. (2009) "Platelet Polyphosphates Are Proinflammatory and Procoagulant Mediators in Vivo," Cell 139:1143-1156.
Mutch et al. (2010) "Polyphosphate Binds with High Affinity to Exosite II of Thrombin," J Thromb Haemost 8:548-555.
Semeraro et al. (2011) Extracellular Histones Promote Thrombin Generation Through Platelet-Dependent Mechanisms: Involvement of Platelet TLR2 and TLR4, Blood 118:1952-1961.
Smith et al. (2010) "Polyphosphate Exerts Differential Effects on Blood Clotting, Depending on Polymer Size," Blood 116:4353-4359.
Yun et al. (2009) "Polyphosphate and Omptins: Novel Bacterial Procoagulant Agents," J Cell Molec Med 13:4146-4153.
Bajzar, L., et al., "TAFI, or plasma procarboxypeptidase B, couples the coagulation and fibrinolytic cascades through the thrombin-thrombomodulin complex"., Journal of Biological Chemistry, vol. 271, No. 28, pp. 16603-16608, (1996).
Bajzar, L., et al., "Thrombin activatable fibrinolysis inhibitor: not just an inhibitor of fibrinolysis"., Crit. Care Med., vol. 32, pp. S320-S324, (2004).
Banner, D.W., et al., "The crystal structure of the complex of blood coagulation factor VIIa with soluble tissue factor"., Nature, vol. 380, pp. 41-46, (1996).

(Continued)

*Primary Examiner* — Karen Cochrane Carlson
*Assistant Examiner* — Natalie Moss
(74) *Attorney, Agent, or Firm* — Lathrop & Gage LLP

(57) ABSTRACT

A fibrin sealant, comprises (a) thrombin, (b) fibrinogen, (c) polyP, and (d) calcium. The thrombin and the fibrinogen are separated prior to application.

20 Claims, 6 Drawing Sheets

(56) References Cited

U.S. PATENT DOCUMENTS

| | | | |
|---|---|---|---|
| 6,528,273 | B2 | 3/2003 | Hawkins |
| 6,706,861 | B2 | 3/2004 | Singh et al. |
| 6,733,985 | B1 | 5/2004 | Lee |
| 6,815,424 | B2 | 11/2004 | Vickery et al. |
| 7,148,067 | B2 | 12/2006 | Morrissey et al. |
| 7,682,808 | B2 * | 3/2010 | Morrissey et al. ............. 435/13 |
| 2001/0004641 | A1 | 6/2001 | Hawkins |
| 2001/0043951 | A1 | 11/2001 | Kim et al. |
| 2002/0012699 | A1 | 1/2002 | Singh et al. |
| 2002/0012958 | A1 | 1/2002 | Wissel et al. |
| 2002/0019021 | A1 | 2/2002 | Kraus |
| 2002/0132370 | A1 | 9/2002 | Lassen et al. |
| 2002/0151646 | A1 | 10/2002 | Kikukawa et al. |
| 2002/0182225 | A1 | 12/2002 | Wang et al. |
| 2003/0064414 | A1 | 4/2003 | Benecky et al. |
| 2003/0153084 | A1 | 8/2003 | Zheng et al. |
| 2003/0211460 | A1 | 11/2003 | Nelsestuen |
| 2004/0037893 | A1 | 2/2004 | Hansen et al. |
| 2004/0043933 | A1 | 3/2004 | Hansen et al. |
| 2004/0084867 | A1 | 5/2004 | Leyland-Jones |
| 2004/0086953 | A1 | 5/2004 | Jenny et al. |
| 2006/0198837 | A1 | 9/2006 | Morrissey et al. |
| 2009/0053288 | A1 * | 2/2009 | Eskridge et al. ............. 424/447 |
| 2010/0143492 | A1 | 6/2010 | Morrissey et al. |
| 2010/0284998 | A1 | 11/2010 | Smith et al. |
| 2010/0297257 | A1 | 11/2010 | Smith et al. |

FOREIGN PATENT DOCUMENTS

| | | |
|---|---|---|
| EP | 0 942 284 | 9/1999 |
| WO | WO 93/07492 | 4/1993 |
| WO | WO 98/44352 | 10/1998 |
| WO | WO 99/15196 | 4/1999 |
| WO | WO 00/62742 | 10/2000 |
| WO | WO 00/64471 | 11/2000 |
| WO | WO 00/70084 | 11/2000 |
| WO | WO 2004/094475 | 11/2004 |
| WO | WO 2004/110462 | 12/2004 |
| WO | WO 2005/031303 | 4/2005 |
| WO | WO 2006/031387 | 3/2006 |
| WO | WO 2006/088741 | 8/2006 |
| WO | WO 2006/096345 | 9/2006 |
| WO | WO 2009/046194 | 4/2009 |
| WO | WO 2009/061697 | 5/2009 |

OTHER PUBLICATIONS

Barrowcliffe, T.W., et al.,"Studies of phospholipid reagents used in coagulation I: Some general properties and their sensitivity to factor VIII"., Thrombosis and Haemostasis, Stuttgart, DE, vol. 46, No. 3, pp. 629-633, (1981).

Bladbjerg, E. M., et al., "In vitro effects of heparin and tissue factor pathway inhibitor on factor VII assays. Possible implications for measurements in vivo after heparin therapy"., Blood Coagulation and Fibrinolysis, vol. 11, No. 8, pp. 739-745, (2000).

Boffa, M. B., et al., "Roles of thermal instability and proteolytic cleavage in regulation of activated thrombin-activable fibrinolysis inhibitor"., J Biol. Chem., vol. 275, pp. 12868-12878, (2000).

Broze, G. J., Jr. "Tissue factor pathway inhibitor"., Thromb. Haemost., vol. 74, pp. 90-93, (1995).

Camerer, E., et al., "Notes on the cell biology of tissue factor"., Haemostasis, vol. 26, pp. 25-30, (1996).

Chikh, G.G., et al., "Attaching histidine-tagged peptides and proteins to lipid-based carriers through use of metal-ion-chelating lipids"., Biochim. Biophys. Acta, vol. 1567, pp. 204-212, (2002).

Cornell, B.A., et al., "Tethered-bilayer lipid membranes as a support for membrane-active peptides"., Biochem. Soc. Trans., vol. 29, pp. 613-617, (2001).

Dano, K., et al., "Plasminogen activators, tissue degradation, and cancer"., Adv. Cancer Res., vol. 44, pp. 139-266, (1985).

Darst, S.A., "A new twist on protein crystallization"., Proc. Natl. Acad. Sci. USA, vol. 95, pp. 7848-7849, (1998).

Docampo, R., et al., "Acidocalcisomes—conserved from bacteria to man"., Nature Rev. Microbiol., vol. 3, pp. 251-261, (2005).

Fiore, M.M., et al., "The biochemical basis for the apparent defect of soluble mutant tissue factor in enhancing the proteolytic activities of factor VIIa"., J. Biol. Chem., vol. 269, pp. 143-149, (1994).

Fiore, M.M., et al., "An unusual antibody that blocks tissue factor/factor VIIa function by inhibiting cleavage only of macromolecular substrates"., Blood, vol. 80, pp. 3127-3134, (1992).

Gemmell, C.H., et al., "Flow as a regulator of the activation of factor X by tissue factor"., Blood, vol. 72, pp. 1404-1406, (1988).

Gemmell, C.H., et al., "The effects of shear rate on the enzymatic activity of the tissue factor-factor VIIa complex"., Microvasc. Res., vol. 40, pp. 327-340, (1990).

Gemmell, C.H., et al., "Utilization of a continuous flow reactor to study the lipoprotein-associated coagulation inhibitor (LACI) that inhibits tissue factor"., Blood, vol. 76, pp. 2266-2271, (1990).

Groves, J.T., et al., "Supported planar bilayers in studies on immune cell adhesion and communication"., J. Immunol. Methods, vol. 278, pp. 19-32, (2003).

Hansen, J-B., et al., "Reduction of factor FVIIa activity during heparin therapy evidence for assay interactions with tissue factor pathway inhibitor and antithrombin"., Thrombosis Research, vol. 100, pp. 389-396, (2000).

International Search Report dated Mar. 1, 2006 for PCT application No. PCT/US2005/029873.

Jeong, S.W., et al., "Synthesis of a polymerizable metal-ion-chelating lipid for fluid bilayers"., J. Org. Chem., vol. 66, No. 14, pp. 4799-4802, (2001).

Jones, D.T., "Do transmembrane protein superfolds exist?", FEBS Letters, vol. 423, pp. 281-285, (1998).

Kent, M.S., et al., "Segment concentration profile of myoglobin adsorbed to metal ion chelating lipid monolayers at the air-water interface by neutron reflection"., Langmuir, vol. 18, No. 9, pp. 3754-3757, (2002).

Kornberg, A. "Inorganic polyphosphate: Toward making a forgotten polymer unforgettable"., Journal of Bacteriology, vol. 177, No. 3, pp. 491-496, (1995).

Kubalek, E.W., et al., "Two-dimensional crystallization of histidine-tagged, HIV-1 reverse transcriptase promoted by a novel nickel-chelating lipid"., J. Structural Biology, vol. 113, pp. 117-123, (1994).

Lauer, S.A., et al., "Development and characterization of Ni-NTA-bearing microspheres"., Cytometry, vol. 48, pp. 136-145, (2002).

Lazarus, R.A., et al., "Inhibitors of Tissue Factor*Factor VIIa for anticoagulant therapy"., Curr. Med. Chem., vol. 11, pp. 2275-2290, (2004).

Linkins, L.A., et al., "New anticoagulant therapy"., Annu. Rev. Med., vol. 56, pp. 63-77, (2005).

Lorenz, B., et al., "Mammalian intestinal alkaline phosphatase acts as highly active exopolyphosphatase"., Biochim. Biophys. Acta, vol. 1547, pp. 254-261, (2001).

Lorenz, B., et al., "Anti-HIV-1 activity of inorganic polyphosphates"., J. Acquir. Immune. Defic. Syndr. Hum. Retrovirol., vol. 14, pp. 110-118, (1997).

Marx, P.F., et al., "Inactivation of active thrombin-activable fibrinolysis inhibitor takes place by a process that involves conformational instability rather than proteolytic cleavage"., J. Biol. Chem., vol. 275, pp. 12410-12415, (2000).

Marx, P.F., et al., "Plasmin-mediated activation and inactivation of thrombin-activatable fibrinolysis inhibitor"., Biochemistry, vol. 41, pp. 6688-6696, (2002).

Morrissey, J.H., "Tissue factor and factor VII initiation of coagulation". In: Colman RW, Hirsh J, Marder VJ, Clowes AW, George JN, editors, Hemostasis and Thrombosis: Basic Principles and Clinical Practice, Philadelphia, Lippincott Williams & Wilkins, pp. 89-101, (2001).

Morrissey, J.H., et al., "Quantitation of activated factor VII levels in plasma using a tissue factor mutant selectively deficient in promoting factor VII activation"., Blood, vol. 81, pp. 734-744, (1993).

Morrissey, J.H., et al., "Factor VIIa-tissue factor: functional importance of protein-membrane interactions"., Thromb. Haemost., vol. 78, pp. 112-116, (1997).

Morrissey, J.H., et al., "Monoclonal antibody analysis of purified and cell-associated tissue factor"., Thromb. Research, vol. 52, pp. 247-261, (1988).

(56) References Cited

OTHER PUBLICATIONS

Mosnier, L.O., et al., "Identification of thrombin activatable fibrinolysis inhibitor (TAFI) in human platelets"., Blood, vol. 101, pp. 4844-4846, (2003).
Nakagaki, T., et al., "Initiation of the extrinsic pathway of blood coagulation: evidence for the tissue factor dependent autoactivation of human coagulation factor VII"., Biochemistry, vol. 30, pp. 10819-10824, (1991).
Nemerson, Y., et al., "Tissue factor accelerates the activation of coagulation factor VII: The role of a bifunctional coagulation cofactor"., Thromb. Res., vol. 40, pp. 351-358, (1985).
Nesheim, M., "Thrombin and fibrinolysis"., Chest, vol. 124, No. 3, pp. 33S-39S, (2003).
Nesheim, M., et al., "Thrombin, thrombomodulin and TAFI in the molecular link between coagulation and fibrinolysis"., Thromb. Haemost, vol. 78, pp. 386-391, (1997).
Neuenschwander, P.F., et al., "Roles of the membrane-interactive regions of factor VIIa and tissue factor. The factor VIIa Gla domain is dispensable for binding to tissue factor but important for activation of factor X"., J. Biol. Chem., vol. 269, pp. 8007-8013, (1994).
Neuenschwander, P.F., et al., "Deletion of the membrane anchoring region of tissue factor abolishes autoactivation of factor VII but not cofactor function. Analysis of a mutant with a selective deficiency in activity"., J. Biol. Chem., vol. 267, pp. 14477-14482, (1992).
Neuenschwander, P.F., et al., "Factor VII autoactivation proceeds via interaction of distinct protease-cofactor and zymogen-cofactor complexes. Implications of a two-dimensional enzyme kinetic mechanism"., J. Biol. Chem., vol. 268, pp. 21489-21492, (1993).
Nilsson, J., et al., "Comparative analysis of amino acid distributions in integral membrane proteins from 107 genomes"., Proteins, vol. 60, pp. 606-616, (2005).
Novotny, W.F., et al., "Platelets secrete a coagulation inhibitor functionally and antigenically similar to the lipoprotein associated coagulation inhibitor"., Blood, vol. 72, pp. 2020-2025, (1988).
Paborsky, L.R., et al., "Lipid association, but not the transmembrane domain, is required for tissue factor activity. Substitution of the transmembrane domain with a phosphatidylinositol anchor"., J. Biol. Chem., vol. 266, pp. 21911-21916, (1991).
Repke, D., et al., "Hemophilia as a defect of the tissue factor pathway of blood coagulation: effect of factors VIII and IX on factor X activation in a continuous-flow reactor"., Proc. Natl. Acad. Sci. USA, vol. 87, pp. 7623-7627, (1990).
Rojkjaer, R., et al., "Activation of the plasma kallikrein/kinin system on endothelial cell membranes"., Immunopharmacology, vol. 43, pp. 109-114, (1999).
Ruf, W., et al., "Phospholipid-independent and -dependent interactions required for tissue factor receptor and cofactor function"., J. Biol. Chem., vol. 266, pp. 2158-2166, (1991).
Ruiz, F.A., et al., "Human platelet dense granules contain polyphosphate and are similar to acidocalcisomes of bacteria and unicellular eukaryotes"., Journal of Biological Chemistry, vol. 279, No. 43, pp. 44250-44257, (2004).
Sandset, P. M., et al., "Heparin induces release of extrinsic coagulation pathway inhibitor (EPI)"., Thromb. Res., vol. 50, pp. 803-813, (1988).
Schneider, M., et al., "Two naturally occurring variants of TAFI (Thr-325 and Ile-325) differ substantially with respect to thermal stability and antifibrinolytic activity of the enzyme"., J. Biol. Chem., vol. 277, pp. 1021-1030, (2002).
Seddon, A.M., et al., "Membrane proteins, lipids and detergents: not just a soap opera"., Biochim. Biophys. Acta., vol. 1666, pp. 105-117, (2004).
Shigematsu, Y., et al., "Expression of human soluble tissue factor in yeast and enzymatic properties of its complex with factor VIIa"., J. Biol. Chem., vol. 267, pp. 267, pp. 21329-21337, (1992).
Smith, S.A., et al., "Properties of recombinant human thromboplastin that determine the International Sensitivity Index (ISI)"., J. Thromb. Haemost, vol. 2, pp. 1610-1616, (2004).
Smith, A., et al., "Properties of recombinant human thromboplastin that determine sensitivity to vitamin K-dependent coagulation factors"., Blood, vol. 104, No. 11, part 1, pp. 155A, 46th Annual meeting of the American Society of Hematology, San Diego, CA, USA, Dec. 4-7, 2004.
Terpe, K., "Overview of tag protein fusions: from molecular and biochemical fundamentals to commercial systems"., Appl. Microbiol. Biotechnol., vol. 60, pp. 523-533, (2003).
Tripodi, A., et al., "Recombinant tissue factor as substitute for conventional thromboplastin in the prothrombin time test"., Thromb. Haemost, vol. 67, pp. 42-45, (1992).
Wallin, E., et al., "Genome-wide analysis of integral membrane proteins from eubacterial, archaean, and eukaryotic organisms"., Protein Sci., vol. 7, pp. 1029-1038, (1998).
Waters, E.K., et al., "Restoring full biological activity to the isolated ectodomain of an integral membrane protein"., Biochemistry, vol. 45, No. 11, pp. 3769-3774, (2006).
Waxman, E., et al., "Human factor VIIa and its complex with soluble tissue factor: Evaluation of asymmetry and conformational dynamics by ultracentrifugation and fluorescence anisotropy decay methods"., Biochemistry, vol. 32, pp. 3005-3012, (1993).
Waxman, E., et al., "Tissue factor and its extracellular soluble domain: The relationship between intermolecular association with factor VIIa and enzymatic activity of the complex"., Biochemistry, vol. 31, pp. 3998-4003, (1992).
Jackson, C.M., "Monitoring oral anticoagulant therapy-INR values for the Owren prothrombin time"., Thromb Haemost, vol. 91, pp. 210-212, (2004).
Stone, M.J., et al., "Recombinant soluble human tissue factor secreted by *Saccharomyces cerevisiae* and refolded from *Escherichia coli* inclusion bodies: glycosylation of mutants, activity and physical characterization"., J. Biochem., vol. 310, pp. 605-614, (1995).
Bader, R., et al., "Multicentric evaluation of a new PT reagent based on recombinant human tissue factor and synthetic phospholipids"., Thrombosis and Haemostasis, vol. 71, No. 3, pp. 292-299, (1994).
Hirsh, J., et al., "American Heart Association/American College of Cardiology Foundation guide to warfarin therapy"., Circulation, vol. 107, pp. 1692-1711, (2003).
Hoots, K., Disseminated Intravascular Coagulation (DIC), Minutes from Jun. 18, 2004 meeting, pp. 1-6.
Kemball-Cook, G., et al., "High-level production of human blood coagulation factors VII and XI using a new mammalian expression vector"., Gene, vol. 139, pp. 275-279, (1994).
Kitchen, S., et al., "Two recombinant tissue factor reagents compared to conventional thromboplastins for determination of international normalised ratio: a thirty-three-laboratory collaborative study"., The Steering Committee of the UK National External Quality Assessment Scheme for Blood Coagulation., Thrombosis and Haemostasis, vol. 76, No. 3, pp. 372-376, (1996).
Kitchen, S., et al., "Standardization of prothrombin time for laboratory control of oral anticoagulant therapy"., Seminars in Thrombosis and Hemostasis, vol. 25, No. 1, pp. 17-25, (1999).
Massignon, D., et al., "Prothrombin time sensitivity and specificity to mild clotting factor deficiencies of the extrinsic pathway: evaluation of eight commercial thromboplastins"., Thrombosis and Haemostasis, vol. 75, No. 4, pp. 590-594, (1996).
Morrison, M., et al., "Discrepant INR values: a comparison between Manchester and Thrombotest reagents using capillary and venous samples"., Clin. Lab. Haemat., vol. 11, No. 4, pp. 393-398, (1989).
Morrissey, J.H., et al., "Molecular cloning of the cDNA for tissue factor, the cellular receptor for the initiation of the coagulation protease cascade"., Cell, vol. 50, pp. 129-135, (1987).
Morrissey, J.H., "Tissue factor: an enzyme cofactor and a true receptor"., Thromb. Haemost., vol. 86, pp. 66-74, (2001).
Neuenschwander, P.F., et al., "Phosphatidylethanolamine augments factor VIIa-Tissue factor activity: Enhancement of sensitivity to phosphatidylserine"., Biochemistry, vol. 34, No. 43, pp. 13988-13993, (1995).
Poller, L., et al., "Minimum lyophilized plasma requirement for ISI calibration"., European Concerted Action on Anticoagulation, Am. J. Clin. Pathol., vol. 109, pp. 196-204, (1998).
Poller, L., "International Normalized Ratios (INR): the first 20 years"., Journal of Thrombosis and Haemostasis, vol. 2, pp. 849-860, (2004).

(56) References Cited

OTHER PUBLICATIONS

Rezaie, A.R., et al., "Expression and purification of a soluble tissue factor fusion protein with an epitope for an unusual calcium-dependent antibody"., Protein Expression and Purification, vol. 3, pp. 453-460, (1992).
Roussi, J., et al., "French multicentric evaluation of recombinant tissue factor (recombiplastin) for determination of prothrombin time"., Thrombosis and Haemostasis, vol. 72, No. 5, pp. 698-704, (1994).
Search from USPTO website dated May 26, 2004, for key words "Factor VII" and thromboplastin.
Search from USPTO website dated May 27, 2004, for key words "Factor VII" and thromboplastin, PGPUB Production Database.
Smith, S.A., et al., "Rapid and efficient incorporation of tissue factor into liposomes"., Journal of Thrombosis and Haemostasis, vol. 2, pp. 1155-1162, (2004).
Testa, S., et al.,"Discrepant sensitivity of thromboplastin reagents to clotting factor levels explored by the prothrombin time in patients on stable oral anticoagulant treatment: impact on the international normalized ratio system"., Haematologica, vol. 87, No. 12, pp. 1265-1273, (2002).
Van Den Besselaar, A.M.H.P., et al., "Annex 3: Guidelines for thromboplastins and plasma used to control oral anticoagulant therapy"., World Health Organization, Technical Report Series, No. 889, pp. 64-93, (1999).
Watson, C., et al., "Recombinant and tissue extract thromboplastins for determination of international normalised ratio in over-anticoagulated patients"., British Journal of Biomedical Science, vol. 56, pp. 123-127, (1999).
Zwaal, R.F., "Membrane and lipid involvement in blood coagulation"., Biochim Biophys Acta, vol. 515, pp. 163-205, (1978).
Abstract of: Smith, S.A., et al.,"Do elevated plasma tissue factor pathway inhibitor (TFPI) levels affect measurement of factor VIIa?"., Blood, vol. 104, issue 11, (2004).
Abstract of: Smith, S.A., et al., "Polyphosphates—A novel modulator of coagulation"., Arteriosclerosis, Thrombosis, and Vascular Biology, Journal of the American Heart Association, Abstracts of the 6th Annual Conference on arteriosclerosis, Thrombosis and Vascular Biology, vol. 25, 4 pages, (2005).
Bouma, B.N., et al., Thrombin-activatable fibrinolysis inhibitor (TAFI, plasma procarboxypeptidase B, procarboxypeptidase R, procarboxypeptidase U)., Journal of Thrombosis and Haemostasis, vol. 1, pp. 1566-1574, (2003).
International Search Report dated Oct. 5, 2006 for PCT application No. PCT/US2006/006642.
Smith, S.A., et al., "Polyphosphate modulates blood coagulation and fibrinolysis"., PNAS, vol. 103, No. 4, pp. 903-908, (2006).
International Search Report dated Dec. 22, 2006 for PCT application No. PCT/US2006/004789.
Radler, U. et al., "Design of supported membranes tethered via metal-affinity ligand-receptor pairs", Biophysical Journal, vol. 79, pp. 3144-3152, (2000).
Shrout, A.L. et al., "Template-directed assembly of receptor signaling complexes", Biochemistry, vol. 42, No. 46, pp. 13379-13385, (2003).
Wolberg, A.S., "Thrombin generation and fibrin clot structure", Blood Reviews, 21, pp. 131-142, (2007).
DiStasio, E., et al., "Cl⁻ Regulates the Structure of the Fibrin Clot", Biophysical Journal, vol. 75, pp. 1973-1979, (1998).
Nair, C.H., et al., "Effect of Temperature, pH and Ionic Strength and Composition on Fibrin Network Structure and Its Development", Thrombosis Research, 42, pp. 809-816, (1986).
Carr Jr., M.E., et al., "Influence of $Ca^{2+}$ on the structure of reptilase-derived and thrombin-derived fibrin gels", Biochem. J., 239, pp. 513-516, (1986).
Lauricella, A.M., et al., "Influence of homocysteine on fibrin network lysis", Blood Coagulation and Fibrinolysis, 17, pp. 181-186, (2006).
Dugan, T.A., et al., "Decorin Modulates Fibrin Assembly and Structure", The Journal of Biological Chemistry, vol. 281, No. 50, pp. 38208-38216, (2006).
Carr Jr., M.E., et al., "Effect of Glycosaminoglycans on Thrombin- and Atroxin-Induced Fibrin Assembly and Structure", Thrombosis Haemostasis, 62, pp. 1057-1061, (1989).
Parise, P. et al. "Effects of low molecular weight heparins on fibrin polymerization and clot sensitivity to t-PA-induced lysis", Blood Coagulation and Fibrinolysis, vol. 4, pp. 721-727, (1993).
Carr Jr., M.E., et al., "Dextran-Induced Changes in Fibrin Fiber Size and Density Based on Wavelength Dependence of Gel Turbidity", Macromolecules, 13, pp. 1473-1477, (1980).
Carr Jr., M.E., "Effect of hydroxyethyl starch on the structure of thrombin- and reptilase-induced fibrin gels", J. Lab. Clin. Med, 108, pp. 556-561, (1986).
Kornberg, A., et al., "Inorganic Polyphosphate: A Molecule of Many Functions", Annu.Rev.Biochem., 68, pp. 89-125, (1999).
Kulaev, I.S., et al., "Metabolism and Function of Polyphosphates in Bacteria and Yeast", Progress Molecular and Subcellular Biology, vol. 23, pp. 27-43, (1999).
Kumble, K.D., et al., "Inorganic Polyphosphate in Mammalian Cells and Tissues", The Journal of Biological Chemistry, vol. 270, No. 11, pp. 5818-5822, (1995).
Hernandez-Ruiz, L., et al., "Inorganic polyphosphate and specific induction of apoptosis in human plasma cells", The Hematology Journal, 91(9), pp. 1180-1186, (2006).
Kawazoe, Y., et al., "Induction of Calcification in MC3T3-E1 Cells by Inorganic Polyphosphate", J. Dent. Res., 83(8), pp. 613-618, (2004).
Han, K.Y., et al., "Polyphosphate blocks tumour metastasis via anti-angiogenic activity", Biochem. J., 406, pp. 49-55, (2007).
Wang, L., et al., "Inorganic polyphosphate stimulates mammalian TOR, a kinase involved in the proliferation of mammary cancer cells", Proc. Natl. Acad. Sci. U.S.A, vol. 100, No. 20, pp. 11249-11254, (2003).
Wolberg, A.S., et al., "Analyzing fibrin clot structure using a microplate reader", Blood Coagulation and Fibrinolysis, vol. 13, No. 6, pp. 533-539, (2002).
Wolberg, A.S., et al., "Elevated prothrombin results in clots with an altered fiber structure: a possible mechanism of the increased thrombotic risk", Blood, vol. 101, No. 8, pp. 3008-3013, (2003).
Yakovlev, S., et al., "Interaction of Fibrin(ogen) with Heparin: Further Characterization and Localization of the Heparin-Binding Site", Biochemistry, 42, pp. 7709-7716, (2003).
Collen, A., et al. "Unfractionated and Low Molecular Weight Heparin Affect Fibrin Structure and Angiogenesis in Vitro", Cancer Research, 60, pp. 6196-6200, (2000).
Carr Jr., M.E, et al. "Size and Density of Fibrin Fibers from Turbidity", Macromolecules, 11, pp. 46-50, (1978).
Mosesson, M.W., "Fibrinogen and fibrin structure and functions", Journal of thrombosis and Haemostasis, 3, pp. 1894-1904, (2005).
Wozniak, G., "Fibrin Sealants in supporting surgical techniques: the importance of individual components", Cardiovascular Surgery, vol. 11, No. S1, pp. 17-21, (2003).
Dickneite, G., et al., "A comparison of fibrin sealants in relation to their in vitro and in vivo properties", Thrombosis Research, 112, pp. 73-82, (2003).
Jackson, M.R., "Fibrin sealants in surgical practice: An overview", The American Journal of Surgery, 182, pp. 1S-7S, (2001).
Aledort, L.M., "Comparative thrombotic event incidence after infusion of recombinant factor VIIa versus factor VIII inhibitor bypass activity", Journal of Thrombosis and Haemostasis, 2, pp. 1700-1708, (2004).
Brody, D.L., et al., "Use of recombinant factor VIIa in patients with warfarin-associated intracranial hemorrhage", Neurocritical Care, 2, pp. 263-267, (2005).
Firozvi, K., et al., "Reversal of low-molecular-weight heparin-induced bleeding in patients with pre-existing hypercoagulable states with human recombinant activated factor VII concentrate", American Journal of Hematology, 81, pp. 582-589, (2006).
Gerotziafas, G.T., et al., "Recombinant factor VIIa partially reverses the inhibitory effect of fondaparinux on thrombin generation after tissue factor activation in platelet rich plasma and whole blood", Thromb. Haemost., 91, pp. 531-537, (2004).

(56) References Cited

OTHER PUBLICATIONS

Hoots, W.K., "Challenges in the Therapeutic use of a "So-Called" Universal Hemostatic Agent: Recombinant factor VIIa", American Society of Hematology, Educ.Program, pp. 426-431, (2006).
Kessler, C.M., "Current and future challenges of antithrombotic agents and anticoagulants: Strategies for reversal of hemorrhagic complications", Seminars in Hematology, 41, pp. 44-50, (2004).
Kornberg, A., et al., "Inorganic polyphosphate: a molecule of many functions", Annu. Rev. Biochem., 68, pp. 89-125, (1999).
Krishnamurthy, G.T., et al., "Clinical comparison of the kinetics of $^{99m}$-Tc-labeled polyphosphate and diphosphonate", Journal of Nuclear Medicine, 15(10), pp. 848-855, (1974).
Kubitza, D., et al., "Safety, pharmacodynamics, and pharmacokinetics of BAY 59-7939—an oral, direct Factor Xa inhibitor—after multiple dosing in healthy male subjects", Eur J Clin Pharmacol, 61, pp. 873-880, (2005).
Lin, J., et al., "The use of recombinant activated factor VII to reverse warfarin-induced anticoagulation in patients with hemorrhages in the central nervous system: preliminary findings", J. Neurosurg., 98, pp. 737-740, (2003).
Lisman, T., et al., "Recombinant factor VIIa reverses the in vitro and ex vivo anticoagulant and profibrinolytic effects of fondaparinux", Journal of Thrombosis and Haemostasis, 1, pp. 2368-2373, (2003).
Luddington, R.J., "Thromboelastography/Thrombelastometry", Clin. Lab. Haemost., 27, pp. 81-90, (2005).
Mathew, P., "Current Opinion on Inhibitor Treatment Options", Seminars in Hematology, 43, pp. S8-13, (2006).
O'Connell, K.A., et al., "Thromboembolic adverse events after use of recombinant human coagulation factor VIIa", JAMA, vol. 295, No. 3, pp. 293-298, (2006).
Oh, J.J., et al., "Recombinant factor VIIa for refractory bleeding after cardiac surgery secondary to anticoagulation with the direct thrombin inhibitor lepirudin", Pharmacotherapy, 26, No. 4, pp. 576-577, (2006).
Ruiz, F.A., et al., "Human platelet dense granules contain polyphosphate and are similar to acidocalcisomes of bacteria and unicellular eukaryotes", Journal of Biological Chemistry, vol. 279, No. 43, pp. 44250-44257, (2004).
Schulman, S., et al., "Anticoagulants and Their Reversal", Transfusion Medicine Reviews, vol. 21, No. 1, pp. 37-48, (2007).
Young, G., et al., "Recombinant activated factor VII effectively reverses the anticoagulant effects of heparin, enoxaparin, fondaparinux, argatroban, and bivalirudin ex vivo as measured using thromboelastography", Blood Coagulation Fibrinolysis, 18, pp. 547-553, (2007).

Poller, L., "Activated partial thromboplastin time (APTT)", Laboratory Techniques in Thrombosis: A Manual ($2^{nd}$ revised edition of ECAT Assay Procedures), Kluwer Academic Publishers, Dordrecht, (1999).
Invitation to Pay Additional Fees and International Search Report for PCT application No. PCT/US2006/004789 dated Oct. 24, 2006.
Smith S.A. et al., "Sensitive fluorescence detection of polyphosphate in polyacrylamide gels using 4',6-diamidino-2-phenylindol", Electrophoresis, vol. 28, No. 19, pp. 3461-3465, (2007).
Colletier, J-P. et al., "Protein encapsulation in liposomes: efficiency depends on interactions between protein and phospholipid bilayer", BMC Biotechnology, vol. 2, pp. 1-8, (2002).
Smith, S.A. et al., "Polyphosphate enhances fibrin clot structure", Blood (ASH Annual Meeting Abstracts), 110: Abstract 403, (2007).
Smith, S.A. et al., "Polyphosphate shortens the clotting time of hemophilic and anticoagulated plasma", Blood (ASH Annual Meeting Abstracts), 110: Abstract 1760, (2007).
Smith, S.A. et al., "The various procoagulant effects of PolyP require different minimal polymer lengths", Blood (ASH Annual Meeting Abstracts), 110: Abstract 1761, (2007).
Dickneite, G. et al., "A comparison of fibrin sealants in relation to their in vitro and in vivo properties", Thrombosis Research, vol. 112, pp. 73-82, (2003).
Luddington, R.J. "Thrombelastography/thromboelastometry", Clin. Lab. Haem., vol. 27, pp. 81-90, (2005).
International Search Report dated Feb. 9, 2009 for PCT application No. PCT/US2008/082225.
Mutch, N.J. et al., "Polyphospates—a novel modulator of Fibrinolysis", Journal of Thrombosis and Haemostasis, vol. 93, No. 4, pp. A21, (2005).
Smith, S.A. et al., "Polyphosphate as a general procoagulant agent", Journal of Thrombosis and Haemostasis, vol. 6, No. 10, pp. 1750-1756, (2008).
Noegel, A. et al., "Isolation of a high molecular weight polyphosphate from *Neisseria gonorrhoeae*", J. Exp. Med., vol. 157, pp. 2049-2060, (1983).
Smith, S.A. et al., "Polyphosphate enhances fibrin clot structure", Blood, vol. 112, No. 7, pp. 2810-2816, (2008).
Allen, D., "Clotting agents buy wounded troops life-saving time", Stars and Stripes, 3 pages, (2003).
International Search Report dated Feb. 10, 2010 for PCT application No. PCT/US2008/078584.
Gibble, et al., "Fibrin glue: the perfect operative sealant?", Transfusion, vol. 30, No. 8, XP002561966, pp. 741-747, (1990).

* cited by examiner

FIBRIN SEALANT

CROSS REFERENCE TO RELATED APPLICATION

This application claims priority to provisional application No. 60/978,009 entitled "Fibrin Sealant" filed 5 Oct. 2007, the entire contents of which are hereby incorporated by reference, except where inconsistent with the present application.

FEDERALLY SPONSORED RESEARCH OR DEVELOPMENT

This application was funded in part under the following research grants and contracts: NIH(NHLBI) Grant No. R01 HL47014. The U.S. Government may have rights in this invention.

BACKGROUND

A schematic of the clotting cascades is shown in FIG. 1(A). In the figure the various clotting factors are indicated by their Roman numeral (i.e., factor VII is indicated by VII). The intrinsic pathway (also referred to as the contact pathway of blood coagulation) is initiated when contact is made between blood and certain artificial surfaces. The extrinsic pathway (also referred to as the tissue factor pathway of blood coagulation) is initiated upon vascular injury which leads to exposure of tissue factor (TF) (also identified as factor III). The dotted arrow represents a point of cross-over between the extrinsic and intrinsic pathways. The two pathways converge at the activation of factor X to Xa. Factor Xa has a role in the further activation of factor VII to VIIa. Active factor Xa hydrolyzes and activates prothrombin to thrombin. Thrombin can then activate factors XI, VIII and V furthering the cascade. Ultimately, the role of thrombin is to convert fibrinogen to fibrin, which forms clots.

Fibrinogen is the most abundant coagulation protein in blood. The formation of a fibrin clot from fibrinogen is the terminal step in the coagulation cascade. Soluble fibrin monomers, which are created when thrombin cleaves fibrinogen, spontaneously polymerize to form a three dimensional network of insoluble fibrin fibrils. Clotting of fibrinogen by thrombin is one of the few steps in the clotting cascade that does not require calcium ions. The resulting fibrin clot structure can be further stabilized via covalent cross-linking of the fibrils through the action of the transglutaminase enzyme, factor XIIIa (FIG. 1 (B)) [26].

Fibrin sealant, also referred to as "fibrin glue" or "fibrin tissue adhesive," is a surgical hemostatic agent derived from plasma coagulation proteins. Fibrin sealants are widely used to control bleeding in a variety of surgical settings, and their use has increased due to the advent of minimally invasive surgical procedures which necessitate meticulous hemostasis for adequate visualization of the surgical field [27]. Fibrin sealants can be used for hemostasis, wound closure, and tissue sealing and have been advocated as the agents that are closest to approaching the ideal operative sealant. In contrast to synthetic adhesives, fibrin sealants have the advantage of being biocompatible and biodegradable, and they are not associated with inflammation, foreign body reactions, tissue necrosis, or extensive fibrosis. Reabsorption of the fibrin clot is achieved during normal wound healing within days to weeks of application, depending on the type of surgery, the proteolytic activity of the treated site, and the amount of sealant used.

Fibrin sealants are typically derived from plasma proteins and contain two primary components: fibrinogen and thrombin. These two components are stored separately and are mixed during application, whereupon the applied mixture forms a fibrin clot on the wound surface to prevent further hemorrhage. The sealant may be applied with a needle, as a spray, or using other devices. When fibrinogen and thrombin are mixed (during application of fibrin sealant to a wound), the fibrinogen component is converted to fibrin monomers. Polymerization of fibrin monomers results in the formation of a semi-rigid fibrin clot that is capable of interacting covalently and non-covalently with tissue structures. The clot may be further stabilized by cross-linking of the fibrin alpha and gamma chains in a reaction catalyzed by activated factor XIII. This cross-linking stimulates adherence of fibroblasts and promotes their normal growth into the clot. By mimicking the latter stages of the physiologic coagulation system, these processes allow fibrin sealants to arrest blood loss and assist the wound healing process.

Most commercially available fibrin sealants contain purified, virally inactivated human fibrinogen and either human or bovine thrombin, optionally with different quantities of factor XIII and anti-fibrinolytic agents (such as bovine aprotinin). Some of the currently available fibrin sealants are summarized in Table 1. Both Tisseel and Beriplast P are marketed as a two-component kit: component one contains lyophilized pooled human fibrinogen/factor XIII concentrate, which is reconstituted with antifibrinolytic solution (aprotinin); and component two is bovine thrombin reconstituted with 40 mM $CaCl_2$. Tisseel is supplied as a lyophilizate or frozen, whereas Beriplast P is supplied as a lyophilizate. The two-component fibrin sealant is usually applied through a double barreled syringe system, which allows simultaneous application of equal volumes of the fibrinogen and thrombin through a blunt-ended needle or spray tip. Virus inactivation of fibrinogen and thrombin is carried out by a variety of methods, including two-step vapor heat at 60° C. and 80° C., pasteurization (liquid solution, 10 hours at 60° C.), or solvent-detergent treatment, with pasteurization, nanofiltration, or exposure to ultraviolet light.

TABLE 1

| | | Composition of fibrin sealants | | | |
| --- | --- | --- | --- | --- | --- |
| Sealant | Form | Human fibrinogen (mg/mL) | Human factor XIII (U/mL) | Human or bovine thrombin (IU/mL) | Bovine aprotinin (KIU/mL) |
| Tisseel ®, Tissucol ® (Duo Baxter-Immuno AG, Austria) | Frozen solution | 70-110 | 10-50 | 500 | 3,000 |

TABLE 1-continued

Composition of fibrin sealants

| Sealant | Form | Human fibrinogen (mg/mL) | Human factor XIII (U/mL) | Human or bovine thrombin (IU/mL) | Bovine aprotinin (KIU/mL) |
|---|---|---|---|---|---|
| Tisseel ®, Tissucol ® (Kit Baxter-Immuno AG, Austria) | Lyophilizate | 70-110 | 10-50 | 500 | 3,000 |
| Tisseel ® (VH Kit Baxter-Immuno AG, USA) | Lyophilizate | 75-115 | | 500 | 3,000 |
| Beriplast P ® (Aventis Behring, Germany) | Lyophilizate | 90 (65-115) | 60 (40-80) | 500 (400-600) | 1,000 |
| Hemaseel ® (APR Haemacure, Canada) (As Tisseel VH Kit Baxter-Immuno) | Lyophilizate | 75-115 | | 500 | 3,000 |
| Quixil ® (Omrix Biopharmaceuticals SA, Israel) | Frozen solution | 60-100 | None | 1,000 | None (tranexamic acid 92 mg/mL) |
| Bolheal ® (Kaketsuken Pharmaceutical, Japan) | Lyophilizate | 80 | 75 | 250 | 1,000 |
| Biocol ® (LFB-Lille, France) | Lyophilizate | 127 | 11 | 558 | 3,000 |
| VIGuard F.S. ® (Vitex: VI Technologies, USA) | Lyophilizate | 50-95 | 3-5 | 200 | None |

Previous studies showed that polyP shortens the clotting time of human plasma by acting at two steps in the clotting cascade: (a) activating the contact pathway of blood clotting, and (b) accelerating the conversion of factor V to Va [20]. Since polyP did not shorten clotting times when thrombin was added to plasma, it was previously concluded that polyP exerts its procoagulant effects at points in the clotting cascade upstream from thrombin.

SUMMARY

In a first aspect, the present invention is a fibrin sealant, comprising (a) thrombin, (b) fibrinogen, (c) polyP, and (d) calcium. The thrombin and the fibrinogen are separated.

In a second aspect, the present invention is a fibrin sealant kit, comprising (I) a first composition comprising (a) thrombin, (II) a second composition comprising (b) fibrinogen, (c) polyP, and (d) calcium, and (III) a fibrin sealant applicator.

In a third aspect, the present invention is a method of controlling bleeding, comprising applying the fibrin sealant to a source of blood loss of a patient. The fibrin sealant comprises (a) thrombin, (b) fibrinogen, (c) polyP, and (d) calcium. The thrombin and the fibrinogen are separated until application.

DEFINITIONS

XIII, FXIII or factor XIII means coagulation factor XIII.
XIIIa, FXIIIa or factor XIIIa means coagulation factor XIIIa.
PolyP$_n$ means a compound of the following formula:

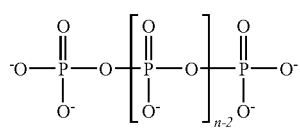

where the value of n is equal to the number of $PO_3$ units in the molecule, and n is at least 3. Polyphosphate (polyP) is a generic term for polyP$_n$, including mixtures, where n of each polyP$_n$ is at least 3. Concentrations of polyphosphate and any polyP$_n$ may be expressed as "phosphate equivalents", which means the concentration of $PO_3$ moieties (for example, 1 µM polyP$_{75}$ is the same as 75 µM phosphate equivalents of polyP$_{75}$). All amounts and concentrations of polyP and polyP$_n$ are expressed herein as phosphate equivalents. Also included are salts, esters, anhydrides of polyphosphate, as well as cyclic polyphosphates.

Thrombin means any protein that exhibits thrombin activity of human thrombin. Thrombin activity of a protein is determined by comparing the concentration of the protein necessary to form the same amount of fibrin clots as 1 nM human thrombin, using the following assay: fibrin clots are formed in 96-well polystyrene microplates using 2.6 mg/mL human fibrinogen in TBS plus thrombin (or the protein being tested for thrombin activity) in TBS added to trigger clot formation in a total volume of 200 µL. Clotting is evaluated by monitoring the change in turbidity ($A_{405}$) for 1 hour at room temperature using a microplate reader. Thrombin may be isolated from blood, or may be made recombinantly. Examples of thrombin include human thrombin, rabbit thrombin and bovine thrombin.

Fibrinogen means any protein that exhibits fibrinogen activity of human fibrinogen. Fibrinogen activity of a protein is determined by comparing the concentration of the protein necessary to form the same amount of fibrin clots as 2.6 mg/mL human fibrinogen, using the following assay: fibrin clots are formed in 96-well polystyrene microplates using fibrinogen (or the protein being tested for fibrinogen activity) in TBS plus 1 nM human thrombin in TBS added to trigger clot formation in a total volume of 200 µL. Clotting is evaluated by monitoring the change in turbidity ($A_{405}$) for 1 hour at room temperature using a microplate reader. Fibrinogen may be isolated from blood, or may be made recombinantly.

Examples of fibrinogen include human fibrinogen, rabbit fibrinogen and bovine fibrinogen.

DETAILED DESCRIPTION

Figure 1A:
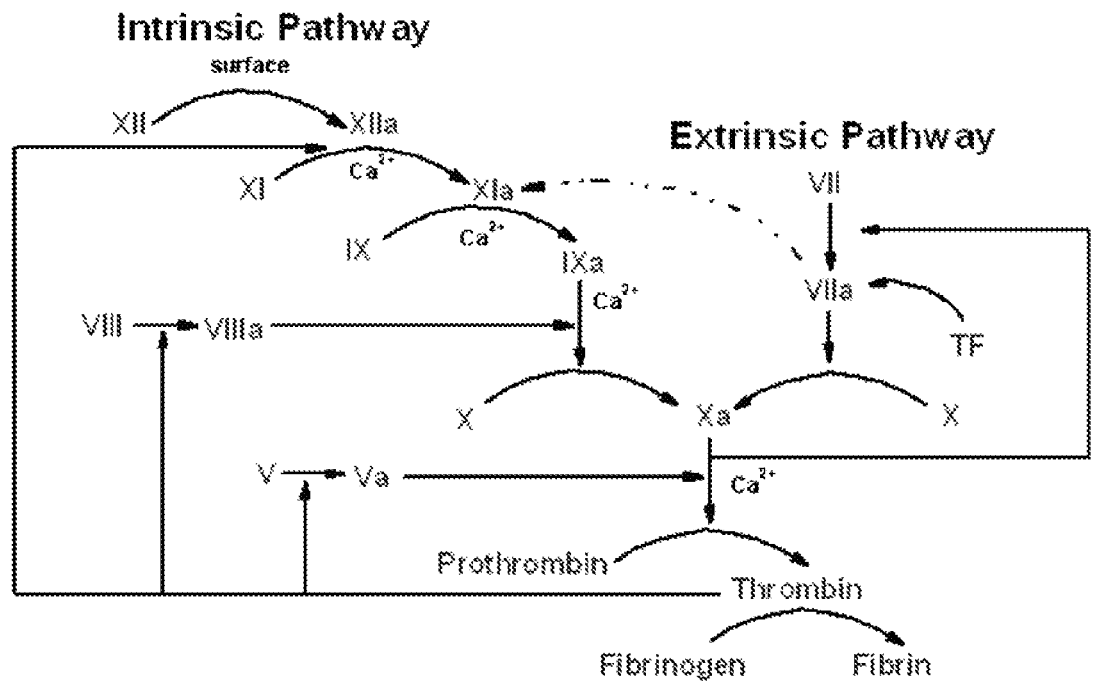
FIG. 1(A) is a schematic of the clotting cascades.
Figure 1B:
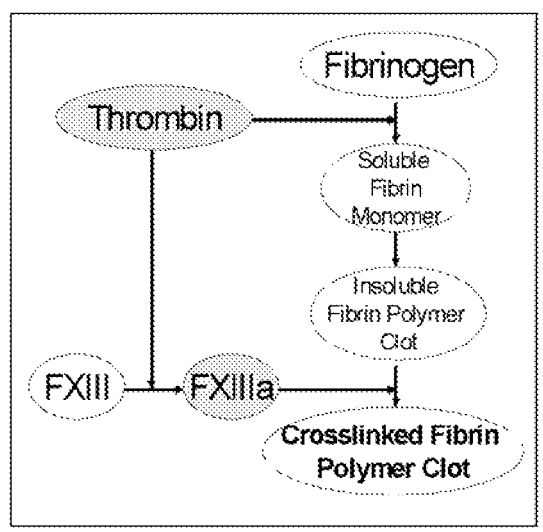
FIG. 1(B) is a schematic of the terminal steps in the blood clotting cascade.

The present invention is based on the discovery that, while polyP does not alter the clotting time induced by thrombin, it does enhance the structure of the resulting fibrin clots. In the present study, fibrin clots were formed by mixing fibrinogen and thrombin. This is a much simpler clotting system than whole plasma, and it also forms the basis for commercially available fibrin sealants, which are widely used as topical hemostatic agents to control bleeding during surgery. PolyP enhanced the structure of fibrin clots by causing the formation of thicker fibrils. Fibrin clots formed in the presence of polyP were also considerably more resistant to fibrinolysis by plasmin. And finally, in experiments using a pig model of surgical bleeding, it has been found that a topical fibrin sealant containing thrombin and fibrinogen was considerably more effective in controlling bleeding when polyP was added to the fibrinogen. Interestingly, polyP was only able enhance fibrin clot structure in the presence of calcium ions. Calcium ions are not required for thrombin to cause the clotting of fibrinogen, although it does have a small effect on the clot structure.

The fibrin sealants of the present invention contain thrombin, fibrinogen, polyP and calcium ions ($Ca^{2+}$). Prior to use, the sealant is provided as two separate components, preferably in the form of a kit, one component containing the thrombin, and the other component containing the fibrinogen. Preferably, the polyP is present in the component containing the fibrinogen, and preferably the calcium ions are also provided in the component containing the fibrinogen. Alternatively, the polyP and the calcium ion may be provided as a third component; or as third and fourth components. Less preferably, the polyP, the calcium ions, or both, may be provided in the component containing thrombin, or both the component contain thrombin and the component containing fibrinogen.

The polyP contains at least 3 $PO_3$ moieties. Preferably, $polyP_n$ with n of at least 25 may be used, for example n=25-1000, more preferably, n=25-100 (including 26, 27, 28, 29, 30, 31, 32, 33, 34, 35, 36, 37, 38, 39, 40, 41, 42, 43 and 44), more preferably n is at least 45, including 45-1000 (including 70, 71, 72, 73, 74, 75, 76, 77, 78, 79 and 80). The amount of polyP or $polyP_n$ per mg of fibrinogen is preferably at least 0.03 micromoles, such as 0.03 to 10 micromole, more preferably 0.04 to 4 micromoles, including 0.05, 0.1, 0.25, 0.5, 1, 2 and 3 micromoles.

Preferably, the calcium ions are provided as calcium chloride. The amount of calcium ions per mg of fibrinogen is preferably at least 0.1 micromoles, such as 0.1 to 100 micromoles, more preferably 0.3 to 10 micromoles, including 0.4, 0.5, 0.75, 1, 2, 5, and 8 micromoles.

Preferably the fibrinogen is mammalian fibrinogen, more preferably rabbit, bovine or human fibrinogen, most preferably human fibrinogen. Preferably, the fibrinogen has been subject to virus inactivation. Preferably, the amount of fibrinogen is at least 1 mg/mL, such as 1 to 500 mg/mL, more preferably 2.5 to 200 mg/mL, most preferably 25 to 125 mg/mL.

Preferably the thrombin is mammalian thrombin, more preferably rabbit, bovine or human thrombin, most preferably human thrombin. Preferably, the thrombin has been subject to virus inactivation, or produced by recombinant means, or both. Preferably, the amount of thrombin per mg of fibrinogen is at least 10 pmoles, such as 10 pmoles to 10 nmoles, more preferably 25 pmoles to 4 nmoles, including 50 pmoles, 100 pmoles, 250 pmoles, 500 pmoles, 1 nmoles, 2 nmoles, and 3 nmoles. Alternatively, the amount of thrombin per mg of fibrinogen is preferably at least 1 IU, such as 1 to 100 IUs, more preferably 4 to 50 IUs, including 5, 10, 20, 25, 30, 35, 40 and 45 IUs.

Optionally, the fibrin sealant may contain a cross-linking agent, such as factor XIII. When factor XIII is used as a cross-linking agent, it is present in an amount, per mg of fibrinogen, of at least 0.01 U, such as 0.01 to 5 U, more preferably 0.05 to 2 U, including 0.1, 0.2, 0.3, 0.4, 0.5, 0.75, 1 and 1.5 U. The cross-linking agent may be present in the component containing thrombin, the component containing fibrinogen, in a separate component, or two or more of these components. Preferably, if factor XIII is present, the factor XIII is mammalian factor XIII, more preferably rabbit, bovine or human factor XIII, most preferably human factor XIII. Preferably, the factor XIII has been subject to virus inactivation, or produced by recombinant means, or both.

Optionally, the fibrin sealant may contain a fibrinolysis inhibitor. Examples include aprotinin and tranexamic acid. Preferably, the fibrin sealant contains aprotinin, in an amount, per mg of fibrinogen, of at least 1 KIU, such as 1 to 500 KIU, more preferably 10 to 100 KIU, including 20, 30, 40, 50, 60, 70, 80 and 90 KIU. The fibrinolysis inhibitor may be present in the component containing thrombin, the component containing fibrinogen, in a separate component, or two or more of these components. Preferably, the fibrinolysis inhibitor has been subject to virus inactivation.

Immediately prior to use, each component of the fibrin sealant should be a liquid. Prior to use, the fibrin sealant may be in a variety of forms, including a frozen solution or as a lyophilizate. The liquid may also contain a pharmaceutically acceptable carrier, such as saline, a buffer solution, or water. Preferably, the fibrin sealant is sterile. A variety of applicators may be used to apply the two-, three-, or more part composition, such as a double-barreled syringe, or a spray applicator. The fibrin sealant can also be applied as drops for separate containers, and mixed at the application site.

EXAMPLES

In Vitro Results (Fibrin Clot Structure)

Figure 2:
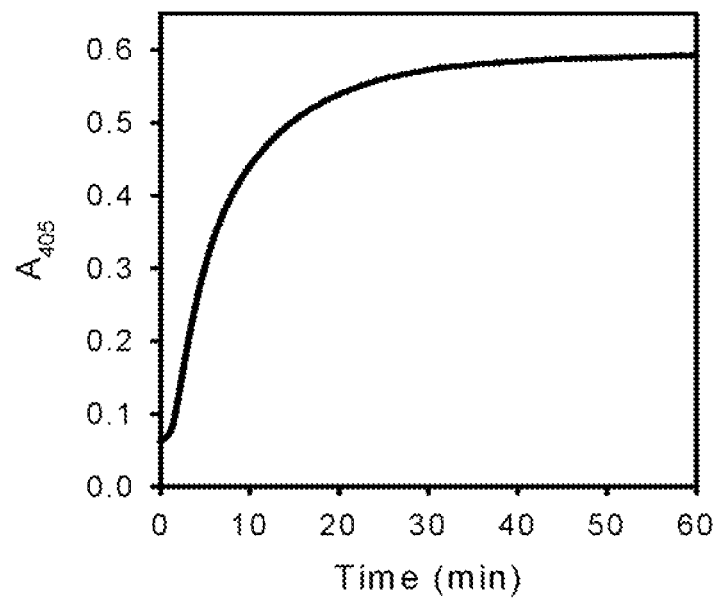
FIG. 2 is a typical graph of the time-dependent change in optical density (measured at 405 nm) observed as a mixture of 2.6 mg/mL fibrinogen and 1 nM thrombin forms a fibrin clot. The final clot turbidity (maximum $A_{405}$) is typically its optical density at 60 minutes.

The in vitro studies reported here utilize a microplate-based method to evaluate the formation of fibrin clots, which are prepared by mixing together purified fibrinogen and thrombin. Once fibrinogen is cleaved to fibrin, the fibrin monomers spontaneously polymerize to yield a three-dimensional gel, or clot. These fibrin polymers scatter visible light, resulting in increased turbidity which can monitored spectrophotometrically to detect clotting. FIG. 2 shows an example of clot formation detected by monitoring the change in optical density.

Figure 3:
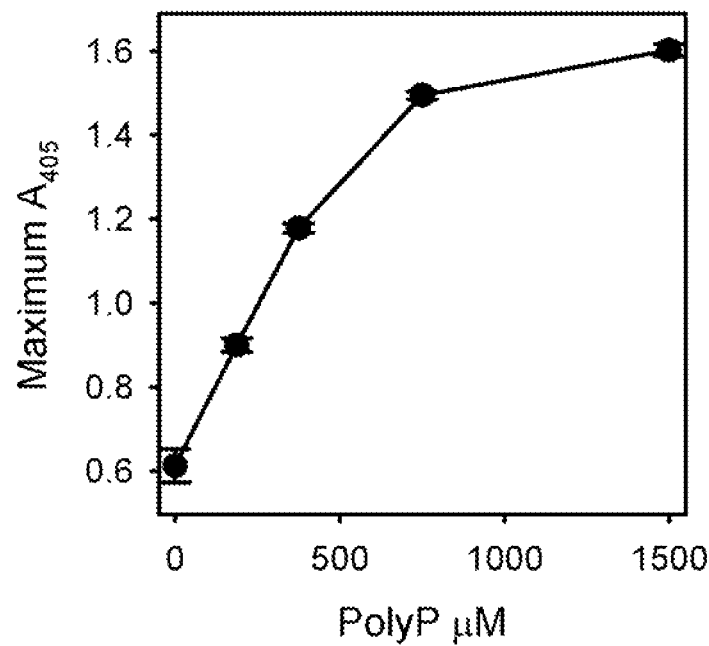
FIG. 3 is a graph showing the enhancement of the final turbidity of fibrin clots formed by mixing 2.6 mg/mL fibrinogen and 8 nM thrombin with various concentrations of polyP. The solution also contained 2.5 mM calcium chloride.
Figure 4:
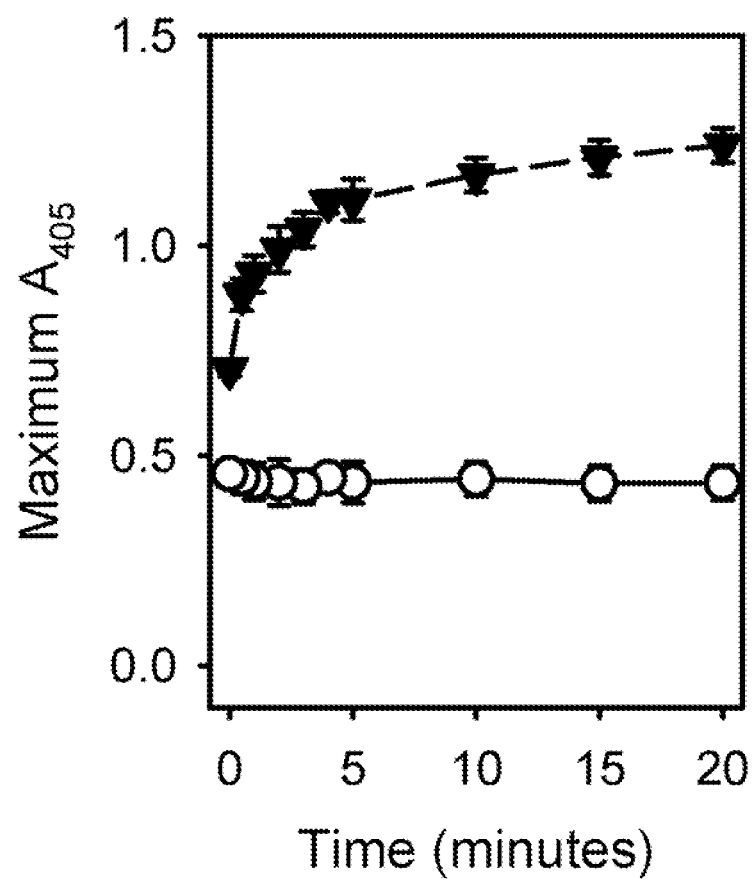
FIG. 4 is a graph of the time dependence of preincubation of fibrinogen with polyP and $Ca^{2+}$ versus final clot turbidity. Reactions contained 2.6 mg/mL fibrinogen preincubated for the indicated times in the presence of 2.5 mM $CaCl_2$ with 1 mM polyP (▼) or without polyP (O), after which clotting was initiated with 8 nM thrombin.
Figure 8:
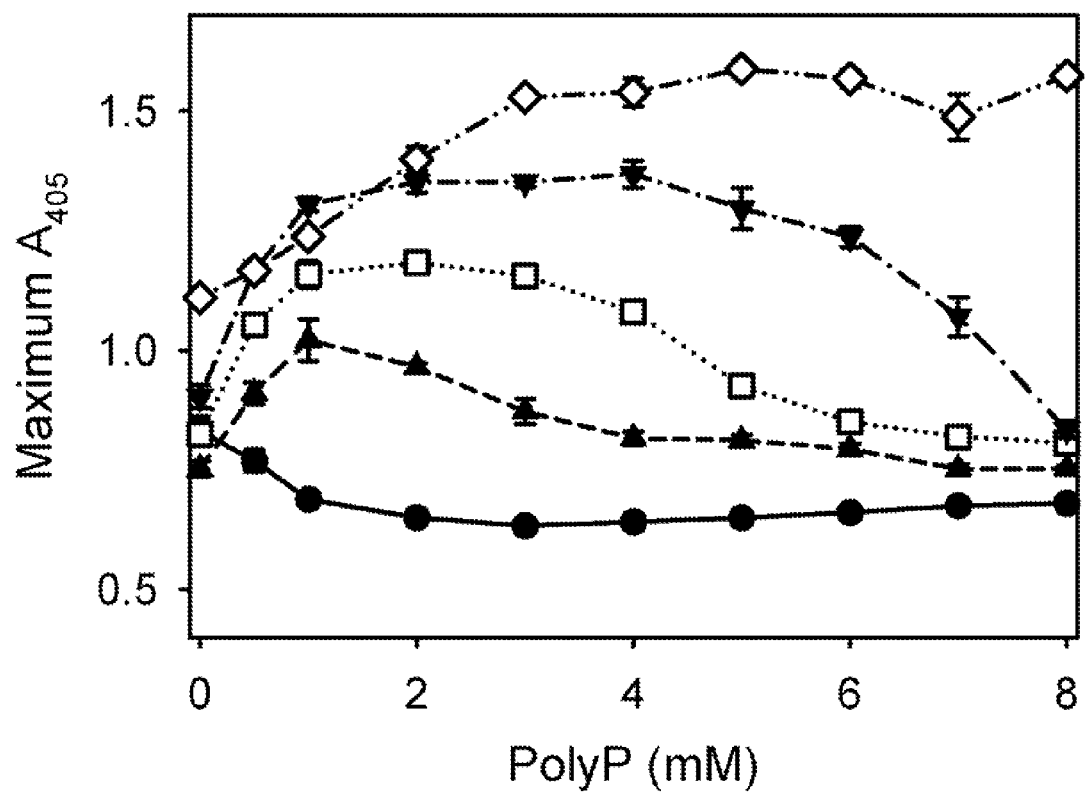
FIG. 8 is a graph of the concentrations of both polyP and $Ca^{2+}$ versus final clot turbidity. Reactions contained 2.6 mg/mL citrate-free fibrinogen, which was preincubated for 15 minutes with $CaCl_2$ and the indicated concentrations of polyP (x axis), after which clotting was initiated with 1 nM thrombin. The $Ca^{2+}$ concentrations were 0 (●), 2 mM (▲), 2.5 mM (□), 3 mM (▼), and 5 mM (◇).

It has now been found that polyP increases the final turbidity of clots formed by the action of thrombin on fibrinogen (FIG. 3). Optimal enhancement of final clot turbidity was observed at approximately 1 mM polyP (expressed as concentration of phosphate monomer), but the optimal polyP concentration also depended on the calcium concentration (FIG. 8). The ability of polyP to enhance clot turbidity requires the presence of calcium ions (FIG. 8). Furthermore, the effect of polyP on final clot turbidity is maximal when polyP has been preincubated for at least 15 minutes with fibrinogen and calcium ions prior to initiating clot formation with thrombin (FIG. 4).

Figure 5:
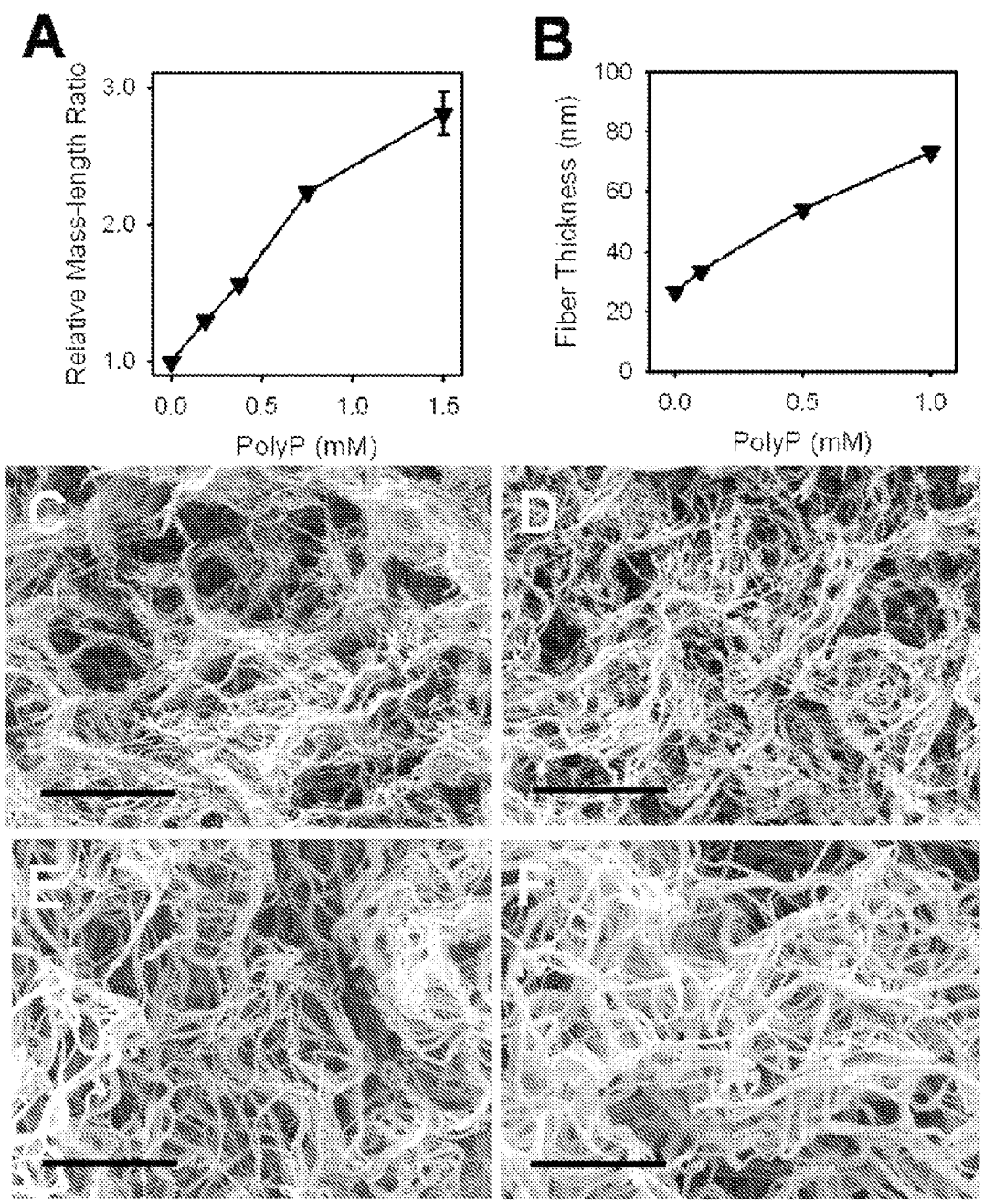
FIG. 5(A) is a graph of the relative mass-length ratios of fibrin clots formed by clotting 2.6 mg/mL fibrinogen with 3 nM thrombin in the presence of 2.5 mM calcium ions and varying concentrations of polyP. The calculated mass-length ratios were normalized to the value obtained in the absence of polyP.
FIG. 5(B) is a graph of fibril thickness measured on scanning electron micrographs of fibrin clots that were formed by clotting 2.6 mg/mL fibrinogen with 3 nM thrombin in the presence of 2.5 mM calcium ions and varying polyP concentrations.
FIGS. 5(C), 5(D), 5(E) and 5(F) are scanning electron micrographs of fibrin clots formed in the presence and absence of polyP. Clots were formed by preincubating 2.6 mg/mL fibrinogen for 15 minutes in the presence of 2.5 mM $CaCl_2$ with (C) No polyP; (D) 100 μM polyP; (E) 500 μM polyP, or (F) 1 mM polyP, after which clotting was initiated in each case with 3 nM thrombin. Bar=2 μm.

It has been found that polyP increases the thickness of the fibrin fibrils. Previous studies of fibrin clot structure have shown that the final optical density of fibrin clots is primarily a function of the thickness of the fibrils formed [25]. It is possible to estimate the mass-length ratios of fibrin fibrils by measuring the optical density of clots at a series of wavelengths of light, using a suitable mathematical analysis of the data [22, 25]. Such analyses of fibrin clots were made by mixing fibrinogen and thrombin in the presence of calcium ions and varying concentrations of polyP, in order to determine the effect of polyP on the mass-length ratio of the fibrils (FIG. 5(A)). These analyses demonstrated that the fibrin fibrils had mass-length ratios that were more than three times larger when clots were made in the presence of 1 mM polyP, compared to fibrin clots formed in the absence of polyP. When fibrin clots formed in the presence of calcium ions and varying polyP concentrations were visualized using scanning electron microscopy, the fibrin fibrils had increased thickness as the polyP concentration increased (FIGS. 5(C-E)). When the fibrin fibril thickness was quantified from such electron micrographs, it was found that polyP resulted in substantially thicker fibrils (FIG. 5(B)).

It should be pointed out that commercial preparations of purified fibrinogen typically contain traces of factor XIII. Therefore, it was conceivable that polyP could be influencing clot structure by modulating the rate or extent of covalent cross-links catalyzed by factor XIIIa. The effect of polyP on final clot turbidity does not appear to result from changing the rate or extent of fibrin cross-linking by factor XIIIa, however. This conclusion comes from studies in which iodoacetamide (a factor XIIIa inhibitor) was added to clotting mixtures to eliminate fibrin cross-linking by factor XIIIa. It was found that polyP enhanced final clot turbidity approximately equally well in the presence or absence of iodoacetamide (data not shown). In additional experiments, the extent of covalent fibrin cross-linking using SDS-PAGE was monitored. The rate of formation of cross-linked fibrin chains appeared to be the same with or without polyP (data not shown).

Figure 6:
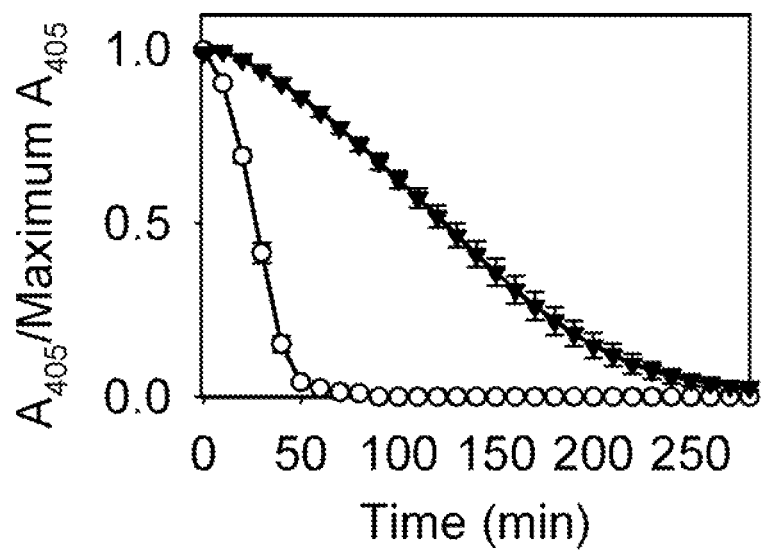
FIG. 6 is a graph of the time course of fibrinolysis of fibrin clots. Fibrinogen (1 mg/mL) was preincubated for 15 minutes in the presence of 2.5 mM $CaCl_2$ with 1 mM polyP (▼) or without polyP (O), after which 8 nM plasmin was added followed immediately by 1 nM thrombin. Fibrin clots were allowed to form for 30 minutes, after which their turbidities were measured. The data are plotted as $A_{405}$ values normalized to the initial $A_{405}$ value for each curve.

It was also found that fibrin clots that were made in the presence of polyP and calcium ions were more resistant to fibrinolysis than clots made in the absence of polyP. In these experiments, clots were formed by mixing purified human fibrinogen, human plasmin, and human thrombin in the presence of calcium ions, with or without polyP. Clot lysis was quantified by measuring the decrease in optical density over time (following a 30 minute initial clot formation). It was found that clots that had been prepared without polyP lysed quickly, while clots prepared with polyP were highly resistant to lysis by plasmin. (FIG. 6)

In Vivo Results (Porcine Splenic Trauma Model)

Figure 7:
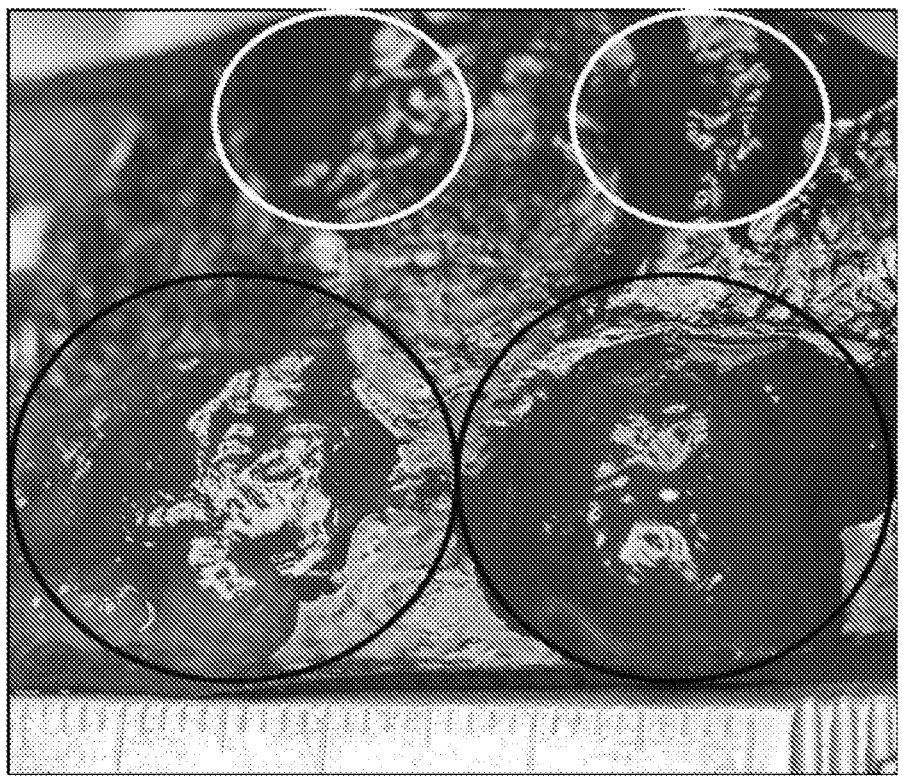
FIG. 7 is a photograph of clots formed after application of a fibrin sealant to spleen surface wounds in a porcine model of surgical bleeding. The lower two wounds (dark circles) were treated with a fibrin sealant prepared with fibrinogen (33.6 mg/mL) that had been preincubated with 1 mM polyP in the presence of 2.5 mM $CaCl_2$, then mixed with an equal volume of thrombin (100 IU/mL). The upper two wounds (white circles) were treated with a fibrin sealant prepared with the same fibrinogen and thrombin concentrations but without polyP.

In preliminary experiments, the ability of polyP to enhance the performance of a fibrin sealant composed of purified fibrinogen and thrombin was evaluated. The fibrinogen component of the experimental fibrin sealant was pre-mixed with calcium ions and polyP, while control fibrinogen preparations were pre-mixed with calcium ions without polyP. Shallow surface wounds were then made on the surface of the spleen of anesthetized pigs, after which 0.3 mL each of the fibrinogen and thrombin solutions were applied to the wound surface and allowed to react with each other. Including polyP in the fibrinogen solution shortened the time to cessation of bleeding in this model: $9.8 \pm 1.0$ minutes with polyP, but $12.3 \pm 1.0$ minutes without polyP (mean±SEM). Adding polyP to the fibrinogen solution also changed the appearance of fibrin clots formed on the wound surfaces. As can be seen in FIG. 7, when the fibrinogen contained polyP (dark circles) the resulting fibrin seals were more opaque, and they mounded up to a greater degree over the wound surface than when fibrinogen did not contain polyP (white circles).

Methods

Purified human fibrinogen in 20 mM citrate pH 7.4 was from Enzyme Research Laboratories (South Bend, Ind.), as were human α thrombin, plasmin, and factor XIII. For some experiments, citrate was removed from fibrinogen immediately prior to use by rapid gel filtration of the fibrinogen solution on Econo-Pac 10DG desalting columns (Bio-Rad, Hercules, Calif.) equilibrated with TBS (50 mM Tris HCl, pH 7.4, 150 mM NaCl, 0.02% NaN3). Fibrinogen concentrations were determined by measuring $A_{280}$, using an extinction coefficient of 1.51 (1 cm path length) for a 1 mg/mL solution of fibrinogen. Unfractionated heparin and $polyP_{75}$, a polyP preparation containing a mean polymer size of approximately 75, were from Sigma Aldrich (St. Louis, Mo.). Concentrations of polyP are expressed in terms of phosphate monomer.

Measurements of Clot Turbidity

Fibrin clots were formed in 96-well polystyrene microplates (Corning Inc., Corning, N.Y.) by first preincubating fibrinogen with polyP in TBS plus the indicated $CaCl_2$ concentrations. (Preincubations of fibrinogen with calcium ions were for 15 minutes unless otherwise stated.) Thrombin in TBS plus the same concentration of $CaCl_2$ was then added to trigger clot formation. Reactant concentrations were typically 2.6 mg/mL fibrinogen, 62.5 pM to 8 nM thrombin, 0 to 8 mM polyP, and 0 to 5 mM $CaCl_2$ in a total volume of 200 μL. In some studies, 0 to 10 U/mL unfractionated heparin or 1 mM iodoacetamide were also included. Clotting was evaluated by monitoring the change in turbidity ($A_{405}$) for varying times (typically, 1 hour) at room temperature using a Spectramax microplate reader (Molecular Devices Corporation, Sunnyvale, Calif.). Clotting times were calculated from these data using SigmaPlot to fit a line to the steepest segment of the absorbance curves and then determining the intersection of this line with the initial baseline $A_{405}$ (representing the lag phase prior to clot formation). Final turbidities ($A_{405}$) of fibrin clots were typically quantified after the clots had matured for 60 minutes.

Fibril Size Determination

Relative fibril mass to length ratios were determined using a modification [21] of the method of Carr and Gabriel [10] for clots with high turbidity. Briefly, fibrin clots were allowed to mature for 2 hours after thrombin addition, after which the absorbance was scanned from 400 to 800 nm on a Spectramax microplate reader. A plot of $1/\tau*\lambda^3$ (y axis) versus $1/\lambda^2$ (x axis) was used to determine the y intercept, the inverse of which is proportional to the mass-length ratio of the fibers [10]. Data were normalized in comparison to clots formed under identical conditions but in the absence of polyP, whose relative mass-length ratios were defined as 1.0 [22].

Scanning Electron Microscopy

Fibrin clots formed as described above for turbidity measurements were allowed to mature for 2 hours after thrombin addition. Clots were washed 4 times in 0.1 M cacodylate, fixed in Karnovsky's gluteraldehyde solution overnight, and then processed by stepwise ethanol gradient, critical point drying, and sputter coating with gold palladium. Clots were observed and photographed in six different representative areas using a scanning electron microscope.

Fibrin Cross-Link Formation

Rates of a and y cross-link formation were studied in clotting reactions carried out as described for turbidity measurements using purified fibrinogen, except that fibrin clots were formed in polypropylene tubes at 37° C. and reactions were stopped at various times by adding an equal volume of 2×SDS sample buffer (100 mM Tris-HCl, 1 mM dithiothreitol, 4% sodium dodecyl sulfate (SDS), 0.02% bromophenol blue, 20% glycerol, pH 6.8) with immediate boiling at 95° C. for 5 minutes. Samples (10 μL) were then subjected to SDS-PAGE using 7.5% polyacrylamide gels and stained with Gelcode (Pierce, Rockford, Ill.) according to the manufacturer's directions.

In Vivo Studies:

Young adult pigs weighing 20-35 kg were anesthetized using intramuscular teletamine/zolazepam/glycopyrolate, followed by intubation and maintenance with inhaled isoflurane. A ventral midline laparotomy was performed and the spleen was externalized. Shallow (approximately 1 mm deep) oval surface wounds measuring approximately 3×5 mm were made using a Metzenbaum scissors. The initial hemorrhage was blotted away to allow visualization, and then the fibrin sealant mixture was applied as follows: 0.3 mL of the fibrinogen solution (containing 33.6 mg/mL fibrinogen, 20 mM sodium citrate, 150 mM NaCl, 20 mM Hepes pH 7.4, 20 mM $CaCl_2$, with or without 100 μg/mL $polyP_{75}$) and 0.3 mL of the thrombin solution (containing 100 U/mL thrombin, 150 mM NaCl, 20 mM Hepes pH 7.4, 5 mM $CaCl_2$) were applied simultaneously to the wound surface using 1 cc syringes with attached 18 gauge needles. For some wounds a 10×10 mm piece of gelfoam was then applied to the wound surface immediately after applying the fibrin sealant mixture. Time to cessation of bleeding was assessed visually. The surgeons were blinded as to which preparations contained polyP, and the wound locations on the spleen were matched for fibrinogen preparations, so the wounds that received polyP were in the same location as wounds that did not. Animal studies were approved by the University of Illinois Institutional Animal Care and Use Committee.

In contrast to the lack of effect on thrombin clotting time, polyP markedly increased final clot turbidity. Clots formed in the presence of polyP were substantially more turbid than clots formed in the absence of polyP, regardless of the amount of thrombin added. Interestingly, the ability of polyP to modulate the turbidity of the resulting fibrin gel was dependent on the $Ca^{2+}$ concentration. In the absence of $Ca^{2+}$, polyP did not increase the turbidity of fibrin clots, but at mM $Ca^{2+}$ concentrations, adding polyP did increase the final turbidity of the fibrin clot (FIG. 8). The polyP concentrations exerting maximal effects on turbidity varied depending on the $Ca^{2+}$ concentration: 1 mM polyP at 2 mM $Ca^{2+}$, 1-2 mM polyP at 2.5 mM $Ca^{2+}$, 2-4 mM polyP at 3 mM $Ca^{2+}$, and 3-8 mM polyP at 5 mM $Ca^{2+}$.

Fibrinogen contains a heparin binding site [23] and heparin increases the turbidity of clots formed from purified fibrinogen and thrombin [24]. Since heparin and polyP are both negatively charged polymers, the turbidity of fibrin clots formed in the presence of polyP was directly compared with the turbidity of clots formed in the presence of heparin. Heparin increased fibrin turbidity in a dose-dependent fashion (examined from 0 to 10 units/mL), but the magnitude of the turbidity increase with heparin was markedly lower than that observed with polyP (data not shown). Further, addition of up to 20 U/mL of unfractionated heparin to reactions containing 500 μM polyP did not reduce the effect of polyP on turbidity. Rather, the mild increase in turbidity due to inclusion of heparin appeared to be additive to the effect of polyP (data not shown). These results suggest that the polyP effect on fibrin clot turbidity is distinct from that of heparin.

The ability of polyP to enhance fibrin clot turbidity required a time-dependent preincubation of fibrinogen, $Ca^{2+}$ and polyP, and was maximal when the three were preincubated together for approximately 10 to 15 minutes (FIG. 4).

Varying the order of addition of these components demonstrated that all three had to be present during the preincubation period in order to achieve maximal increases in clot turbidity (not shown).

The fact that polyP enhanced clot turbidity only in the presence of $Ca^{2+}$ suggested that this enhancement might be associated with factor XIIIa cross-linking activity, which is also calcium-dependent. Since purified fibrinogen may contain small amounts of contaminating factor XIII, some degree of covalent crosslinking is likely to occur during the formation of fibrin gels. However, it was observed that polyP still increased fibrin clot turbidity when preactivated factor XIIIa was added to the clotting mixtures (data not shown). Furthermore, the transglutaminase inhibitor, iodoacetamide, failed to antagonize the enhancement of final clot turbidity by polyP (data not shown). Finally, SDS-PAGE analysis failed to identify any impact of polyP on the time-dependent disappearance of the fibrinogen γ chain, or the appearance of γ-γ dimers or α polymers (data not shown). These results indicated that the increase in fibrin gel turbidity associated with polyP was not dependent on the cross-linking activity of factor XIIIa.

Representative images of fibrin clots made from purified fibrinogen, $Ca^{2+}$ and thrombin (±polyP) are presented in FIGS. 5(C), 5(D), 5(E) and 5(F). Clots made in the presence of polyP had markedly thicker fibers than clots made without polyP. Mean fibril thickness (±standard error) for clots made in the absence of polyP was 26.5±0.7 nm. Mean fibril thicknesses for clots made in the presence of polyP were: 33.6±1.0 nm with 100 μM polyP; 54.2±1.3 nm with 500 μM polyP; and 73.4±1.5 nm with 1 mM polyP.

REFERENCES

1. Wolberg A S. Thrombin generation and fibrin clot structure. Blood Rev. 2007; 21:131-142.
2. Di Stasio E, Nagaswami C, Weisel J W, Di Cera E. Cl⁻ regulates the structure of the fibrin clot. Biophys. J. 1998; 75:1973-1979.
3. Nair C H, Shah G A, Dhall D P. Effect of temperature, pH and ionic strength and composition on fibrin network structure and its development. Thromb. Res. 1986; 42:809-816.
4. Morrissey J H, et al. COAGULATION AND FIBRINOLYTIC CASCADES MODULATOR, WO 2006/096345 A2, 14 Sep. 2006.
5. Carr M E, Jr., Gabriel D A, McDonagh J. Influence of $Ca^{2+}$ on the structure of reptilase-derived and thrombin-derived fibrin gels. Biochem. J. 1986; 239:513-516.
6. Lauricella A M, Quintana I, Castanon M, Sassetti B, Kordich L. Influence of homocysteine on fibrin network lysis. Blood Coagul. Fibrinolysis 2006; 17:181-186.
7. Dugan T A, Yang V W, McQuillan D J, Hook M. Decorin modulates fibrin assembly and structure. J. Biol. Chem. 2006; 281:38208-38216.
8. Carr M E, Jr., Powers P L. Effect of glycosaminoglycans on thrombin- and atroxin-induced fibrin assembly and structure. Thromb. Haemost. 1989; 62:1057-1061.
9. Parise P, Morini M, Agnelli G, Ascani A, Nenci G G. Effects of low molecular weight heparins on fibrin polymerization and clot sensitivity to t-PA-induced lysis. Blood Coagul. Fibrinolysis 1993; 4:721-727.
10. Carr Jr M E, Gabriel D A. Dextran-induced changes in fibrin fiber size and density based on wavelength dependence of gel turbidity. Macromolecules 1980; 13:1473-1477.
11. Carr M E, Jr. Effect of hydroxyethyl starch on the structure of thrombin- and reptilase-induced fibrin gels. J. Lab Clin. Med. 1986; 108:556-561.
12. Kornberg A, Rao N N, Ault-Riche D. Inorganic polyphosphate: a molecule of many functions. Annu. Rev. Biochem. 1999; 68:89-125.
13. Kulaev I S, Kulakovskaya T V, Andreeva N A, Lichko L P. Metabolism and function of polyphosphates in bacteria and yeast. Prog. Mol. Subcell. Biol. 1999; 23:27-43.
14. Kumble K D, Kornberg A. Inorganic polyphosphate in mammalian cells and tissues. J. Biol. Chem. 1995; 270: 5818-5822.
15. Hernandez-Ruiz L, Gonzalez-Garcia I, Castro C, Brieva J A, Ruiz F A. Inorganic polyphosphate and specific induction of apoptosis in human plasma cells. Haematologica 2006; 91:1180-1186.
16. Kawazoe Y, Shiba T, Nakamura R et al. Induction of calcification in MC3T3-E1 cells by inorganic polyphosphate. J. Dent. Res. 2004; 83:613-618.
17. Han K Y, Hong B S, Yoon Y J et al. Polyphosphate blocks tumour metastasis via anti-angiogenic activity. Biochem. J. 2007; 406:49-55.
18. Wang L, Fraley C D, Faridi J, Kornberg A, Roth R A. Inorganic polyphosphate stimulates mammalian TOR, a kinase involved in the proliferation of mammary cancer cells. Proc. Natl. Acad. Sci. U.S.A 2003; 100:11249-11254.
19. Ruiz F A, Lea C R, Oldfield E, Docampo R. Human platelet dense granules contain polyphosphate and are similar to acidocalcisomes of bacteria and unicellular eukaryotes. J. Biol. Chem. 2004; 279:44250-44257.
20. Smith S A, Mutch N J, Baskar D et al. Polyphosphate modulates blood coagulation and fibrinolysis. Proc. Natl. Acad. Sci. U.S.A 2006; 103:903-908.
21. Wolberg A S, Gabriel D A, Hoffman M. Analyzing fibrin clot structure using a microplate reader. Blood Coagul. Fibrinolysis 2002; 13:533-539.
22. Wolberg A S, Monroe D M, Roberts H R, Hoffman M. Elevated prothrombin results in clots with an altered fiber structure: a possible mechanism of the increased thrombotic risk. Blood 2003; 101:3008-3013.
23. Yakovlev S, Gorlatov S, Ingham K, Medved L. Interaction of fibrin(ogen) with heparin: further characterization and localization of the heparin-binding site. Biochemistry 2003; 42:7709-7716.
24. Collen A, Smorenburg S M, Peters E et al. Unfractionated and low molecular weight heparin affect fibrin structure and angiogenesis in vitro. Cancer Res. 2000; 60:6196-6200.
25. Carr M E, Jr., Hermans J. Size and density of fibrin fibers from turbidity. Macromolecules 1978; 11:46-50.
26. Mosseson M W, Fibrinogen and fibrin structure and functions. J Thromb Haemost 3: 1894-1904, 2005.
27. Wozniak G. Fibrin Sealants in supporting surgical techniques: the importance of individual components. Cardiovascular Surgery 11:17-21, 2003.
28. Dickneite G. et al. A comparison of fibrin sealants in relation to their in vitro and in vivo properties. Thrombosis Research 112: 73-82, 2003.
29. Jackson M. R. Fibrin sealants in surgical practice: An overview. The American Journal of Surgery 182:1S-7S, 2001.
30. Morrissey J H, et al. COAGULATION AND FIBRINOLYTIC CASCADES MODULATOR, U.S. Patent Application Publication, Pub. No. US 2006/0198837 A1, Sep. 7, 2006.

What is claimed is:
1. A fibrin sealant composition, comprising:
(a) a first container containing a first composition comprising isolated or recombinant thrombin, and

(b) a second container containing a second composition comprising: purified or recombinant fibrinogen, polyphosphate (polyPn), wherein n is at least 25, and calcium.

2. The fibrin sealant composition of claim 1, wherein n is 25-1000.

3. The fibrin sealant composition of claim 1, further comprising a cross-linking agent.

4. The fibrin sealant composition of claim 3, wherein the cross-linking agent is factor XIII.

5. The fibrin sealant composition of claim 1, further comprising a fibrinolysis inhibitor.

6. The fibrin sealant composition of claim 1, wherein the fibrinogen is present in an amount between 2.5 to 200 mg/mL.

7. A fibrin sealant kit, comprising:
(I) a first container containing a first composition comprising isolated or recombinant thrombin,
(II) a second container containing a second composition, stored separate from the first composition, comprising: purified or recombinant fibrinogen, polyphosphate (polyPn), wherein n is at least 25, and calcium, and
(III) a fibrin sealant applicator.

8. The fibrin sealant kit of claim 7, wherein n is 25-1000.

9. The fibrin sealant kit of claim 7, further comprising a cross-linking agent.

10. The fibrin sealant kit of claim 9, wherein the cross-linking agent is factor XIII.

11. The fibrin sealant kit of claim 7, further comprising a fibrinolysis inhibitor.

12. The fibrin sealant kit of claim 7, wherein the fibrin sealant applicator is a double barreled syringe.

13. The fibrin sealant kit of claim 7, wherein the fibrin sealant applicator is a spray applicator.

14. The fibrin sealant composition of claim 1, wherein the fibrinogen is recombinant fibrinogen.

15. The fibrin sealant composition of claim 1, wherein the first composition and second composition are liquid.

16. The fibrin sealant composition of claim 1, wherein the fibrinogen, polyPn and calcium have been incubated for at least 15 minutes.

17. The fibrin sealant kit of claim 7, wherein the fibrinogen is recombinant fibrinogen.

18. The fibrin sealant kit of claim 7, wherein the first composition and second composition are liquid.

19. The fibrin sealant kit of claim 7, wherein the fibrinogen, polyPn and calcium have been incubated for at least 15 minutes.

20. The fibrin sealant kit of claim 7, wherein the fibrinogen is present in an amount between 2.5 to 200 mg/mL.

* * * * *